(12) United States Patent
Masse

(10) Patent No.: US 7,997,025 B1
(45) Date of Patent: Aug. 16, 2011

(54) ALGAE PRODUCTION AND HARVESTING APPARATUS

(75) Inventor: Arthur W. P. Masse, Hobe Sound, FL (US)

(73) Assignee: Trinitas, LLC, Hobe Sound, FL (US)

( * ) Notice: Subject to any disclaimer, the term of this patent is extended or adjusted under 35 U.S.C. 154(b) by 0 days.

(21) Appl. No.: 12/466,008

(22) Filed: May 14, 2009

(51) Int. Cl.
   *A01H 13/00* (2006.01)
(52) U.S. Cl. .......................................... 47/1.4
(58) Field of Classification Search ............ 47/1.4
   See application file for complete search history.

(56) References Cited

U.S. PATENT DOCUMENTS

| | | | |
|---|---|---|---|
| 2,815,607 A * | 12/1957 | Schroeder | 47/1.4 |
| 4,324,067 A | 4/1982 | Kessler | |
| 4,676,956 A | 6/1987 | Mori | |
| 4,724,214 A | 2/1988 | Mori | |
| 4,892,818 A | 1/1990 | Ramp | |
| 4,900,678 A | 2/1990 | Mori | |
| 4,952,511 A * | 8/1990 | Radmer | 435/292.1 |
| 5,104,803 A | 4/1992 | Delente | |
| 5,162,051 A | 11/1992 | Hoeksema | |
| 5,772,887 A | 6/1998 | Noah et al. | |
| 6,572,770 B1 | 6/2003 | Stewart, III et al. | |
| 7,176,024 B2 | 2/2007 | Branson et al. | |
| 7,425,441 B2 | 9/2008 | Broneske et al. | |
| 2003/0059932 A1* | 3/2003 | Craigie et al. | 435/292.1 |
| 2003/0073231 A1* | 4/2003 | Dutil | 435/292.1 |
| 2003/0228684 A1 | 12/2003 | Burbidge et al. | |
| 2005/0239182 A1 | 10/2005 | Berzin | |
| 2005/0255584 A1 | 11/2005 | Broneske et al. | |
| 2006/0035370 A1* | 2/2006 | Lee et al. | 435/292.1 |
| 2007/0092962 A1 | 4/2007 | Sheppard | |
| 2007/0094926 A1 | 5/2007 | Branson et al. | |
| 2007/0113474 A1 | 5/2007 | Everett et al. | |
| 2007/0128707 A1 | 6/2007 | Rorrer et al. | |
| 2007/0155006 A1 | 7/2007 | Levin | |
| 2008/0094843 A1 | 4/2008 | Zweig et al. | |
| 2008/0135475 A1 | 6/2008 | Limcaco | |
| 2008/0220515 A1 | 9/2008 | McCall | |
| 2008/0254529 A1 | 10/2008 | Freeman | |
| 2009/0023199 A1 | 1/2009 | Gal | |
| 2010/0151540 A1* | 6/2010 | Gordon et al. | 435/134 |
| 2010/0261260 A1* | 10/2010 | Morgan | 435/257.3 |

FOREIGN PATENT DOCUMENTS

| | | |
|---|---|---|
| JP | 5277357 | 10/1993 |
| JP | 7023767 | 1/1995 |
| WO | 2007070452 | 6/2007 |
| WO | 2007098150 | 8/2007 |
| WO | 2008028143 | 3/2008 |
| WO | 2008097845 | 8/2008 |
| WO | 2009002772 | 12/2008 |
| WO | WO 2010132812 A2 * | 11/2010 |

* cited by examiner

*Primary Examiner* — Francis T Palo
(74) *Attorney, Agent, or Firm* — Jetter & Associates, P.A.

(57) ABSTRACT

A photo-bioreactor module adapted for stacking a plurality of such modules for producing algal bioproducts includes at least an upper and a lower light-transmitting member each having a plurality of openings. The upper and lower light-transmitting members are spaced apart from one another and at least one of the upper and lower light-transmitting members includes at least one light connection terminal for coupling in light from a light source and transmitting the light laterally. A plurality of photobioreactor conduits each extending from respective openings in the upper and lower light-transmitting member define algae containment interior spaces, wherein the plurality of photobioreactor conduits contact the upper and a lower light-transmitting members along areas of contact. The light transmitted laterally by the upper and lower light-transmitting members couples into the plurality of photobioreactor conduits along the areas of contact.

23 Claims, 12 Drawing Sheets

ALGAE PRODUCTION AND HARVESTING APPARATUS

FIELD OF THE INVENTION

This disclosure generally relates to production of biofuels. More particularly, this disclosure relates to algae production and harvesting, which is suitable for the mass harvesting of algae bioproduct in sufficient quantities to produce algal fuel.

BACKGROUND

Fossil fuels, such as coal and gasoline, currently provide most of the energy needs of the world—including the United States. Moreover, the demand for fossil fuels has steadily increased over the years. At the time of the Oil Embargo of 1973, the U.S. net oil import rate was only one-third of total consumption, whereas today the U.S. net oil import rate approaches two-thirds of total consumption. With the U.S. oil consumption rate increasing by approximately 11 percent over the past ten years, and with crude oil spot prices have been recorded well over $140 per barrel, the U.S. economy is faced with a fuel bill approaching $700 billion over the next decade.

Because of the diminishing reserves and increasing costs of fossil fuels, as well as the damaging effects fossil fuels can have on the environment, alternative energy sources that are renewable and less damaging to the environment are currently being developed. Alternative energy sources generally include natural gas, wind energy, hydroelectric power, solar energy, hydrogen, nuclear energy and biofuels.

Although natural gas is a fossil fuel that burns cleaner than gasoline, it produces carbon dioxide—the primary greenhouse gas. Wind energy, one of the oldest and cleanest forms of energy, is unsightly and noisy. Hydroelectric power, an old and well-developed energy source, has a limited capacity for expansion. All energy (other than nuclear energy) is ultimately derived from solar energy, which can also be gathered directly using photoelectric cells. Hydrogen has proven to be a viable fuel source for vehicles, with the advent of fuel cells. However, use of hydrogen as an energy source poses problems with respect to its production, storage and distribution. Nuclear energy includes nuclear fission, which is very costly and generates toxic waste, and nuclear fusion, which is clean but has proven unworkable.

Biofuel is commonly defined as a solid, liquid or gas fuel derived from recently living organisms, including plants, animals and their byproducts. It is a renewable energy source based on the carbon cycle, unlike other natural resources such as petroleum, coal and nuclear fuels. Biofuels can be obtained from wood, single- and multi-cellular plant materials, animal excrement and bacteria. Ethanol is one type of biofuel that, combined with gasoline, is widely used in the transportation industry. Since biofuels can also be derived from plant oils, algae-derived biofuels have proven to be a promising alternative energy source. However, various obstacles have thwarted the large-scale manufacture and use of algal biofuels.

A primary obstacle inherent to conventional algal fuel production is the inability to produce and harvest algae in sufficient quantities to provide enough algal fuel to serve the energy needs of civilization. Utilizing existing methods, production of algal fuel in sufficient quantities would require growing algae in large production ponds or photo-bioreactors, each of which is limited by production and economic inefficiencies. It is estimated that approximately 200,000 hectares (approximately 450,000 acres or 780 square miles) of production pond surface area would be required to produce a quantity of algal biodiesel sufficient to replace the quantity of oil currently consumed each year in the United States.

Algae feedstock grown in open pond systems are subject to many systemic inefficiencies and challenges, some of which are also common to both open and closed system photobioreactor systems. Some of these challenges include the controllability of spectrum, intensity and duration of light cycles; temperature controls or seasonal temperature variations; contamination by hostile windborne particulate; and the cost of harvesting, transport, pre-treatment and storage, to name a few. These and other related challenges of conventional algae farming methods effectively limit the commercial viability of algal fuels.

Closed system photo-bioreactors, another conventional algal fuel production system, suffer from many of the same limitations, drawbacks and disadvantages, associated with open pond systems. For example, known closed photo-bioreactor systems preclude adequate control of light quantity, spectrum, duration and cycle. Additional issues include land area requirements, supporting and foundational structure requirements for large scale production applications, and harvesting inefficiencies. While closed system photo-bioreactors overcome, or substantially mitigate, many of the environmental and biological issues associated with open pond systems, they have not yet achieved an adequate level of efficiency required to produce algal biomass in quantities sufficient to reduce national dependence on foreign oil.

Accordingly, there is an unmet need for an algae bioproduct production and harvesting apparatus suitable for the mass production and harvesting of algae. What is needed is an apparatus that overcomes the aforementioned limitations, disadvantages and drawbacks, concomitant with open pond systems, closed-apparatus photo-bioreactors, and other known systems. It would be desirable to provide such an apparatus that enables greatly improved control over algae light exposure variables, including, for example, control over light cycle, light quantity, light spectrum and light duration. It would be further desirable to provide such an apparatus that also enables and facilitates precise monitoring and control of other variables that are known to affect algae growth rate, including, for example, algae temperature exposure, nutrient levels, and gas (e.g., $O_2$ and $CO_2$) levels. In order to address the aforementioned land requirement issues associated with existing open pond systems and closed system photo-bioreactors, it would be highly desirable to provide an apparatus having a structural configuration requiring a smaller footprint vis-à-vis existing systems. In short, it would be highly desirable to provide an apparatus that is low cost, easy to maintain, easy to reproduce, and that enables an operator to precisely control all aspects of the Calvin Cycle in order to maximize production and harvesting volume and efficiency, regardless of the desired strain of algae being grown.

SUMMARY OF THE INVENTION

This disclosure is generally directed to an algae production and harvesting apparatus that is suitable for the mass production and harvesting of algae bioproducts in sufficient quantities to produce algal fuel. The apparatus is vertically scalable and, accordingly, has the benefit of a small footprint vis-à-vis other known algae bioproduct production and harvesting systems and methods. The apparatus can provides the ability to control characteristics of temperature, light and other factors known to affect the rate of growth of algae, in order to maximize production efficiency. The apparatus generally incorporates relatively low-cost components arranged in a manner that facilitates efficient deployment and subsequent repair. The unique vertical arrangement disclosed herein takes advantage of natural fluid dynamics for supplementary apparatus structural support.

In one implementation, a vertically-stackable modular apparatus for algae bio-product production and harvesting comprises at least an upper and a lower light-transmitting member each having a plurality of openings, wherein the upper and lower light-transmitting members are spaced apart from one another and at least one of the upper and lower light-transmitting members includes at least one light connection terminal for coupling in light from a light source and transmitting the light laterally. A plurality of photobioreactor conduits extending from respective openings in the upper and the lower light-transmitting member each define algae containment interior spaces, wherein the plurality of photobioreactor conduits contact the upper and lower light-transmitting members along areas of contact. The light transmitted laterally by the upper and lower light-transmitting members couples into the plurality of photobioreactor conduits along the areas of contact.

In another aspect, the algae containment structure can comprise a light-transmitting unitary structure having a plurality of parallel linear channels extending through the unitary structure in such a manner that adjacent channels share a sidewall. Furthermore, each linear channel may be selected having a pre-determined uniform cross-sectional area for maximizing growth of a particular algae strain.

In another aspect, the algae containment structure can include a plurality of individual light-transmitting linear conduit members, each defining an interior conduit space. Each conduit member can be chosen having a uniform cross-sectional area for maximizing growth of a particular algae strain.

In another aspect, the linear channels and linear conduit members can have any of a number of different cross-sectional geometries, including, for example, circular, elliptical, triangular, rectangular and hexagonal.

In another aspect, the light transmitter can include a plurality of light transmitting strands communicating light from the light source to individual linear conduit members.

In another aspect, the light transmitter can include a horizontally-disposed light transmitting panel having a plurality of apertures for receiving the respective plurality of linear conduit elements therethrough, wherein the panel transmits light from the light source to the linear conduit members, and provides structural support for the conduit members.

In another aspect, the photo-bioreactor module can include a structural attachment mechanism for enabling secure vertical stacking of multiple photo-bioreactor modules, as well as an optional module lifting structure for facilitating vertical hoisting of an upper module from an underlying lower module.

In another aspect, a gasket can be provided interposed between stacked modules to ensure sealed communication between aligned interior spaces extending through the stacked modules.

In another aspect, a product collecting vessel can be provided in communication with the photobioreactor module for collecting algae biomass, excretions, and other algae derivative product. Optionally, a product transfer assembly, which may be in the form of conduits, can provide fluid communication between the photo-bioreactor module and the collecting vessel.

In another aspect, a processor may be disposed in fluid communication with the collecting vessel for processing the algae biomass, excretions, and other algae derivative product.

In another aspect, the apparatus includes known components enabling monitoring of, and control over, other factors known to affect algae growth rate, such as $CO_2$ concentration, $O_2$ levels, and nutrient levels, for example.

BRIEF DESCRIPTION OF THE DRAWINGS

Disclosed embodiments will hereinafter be described, in conjunction with the appended drawings, provided to illustrate and not to limit the appended claims, where like designations denote like elements, and in which:

DETAILED DESCRIPTION OF THE PREFERRED EMBODIMENTS

Figure 1:
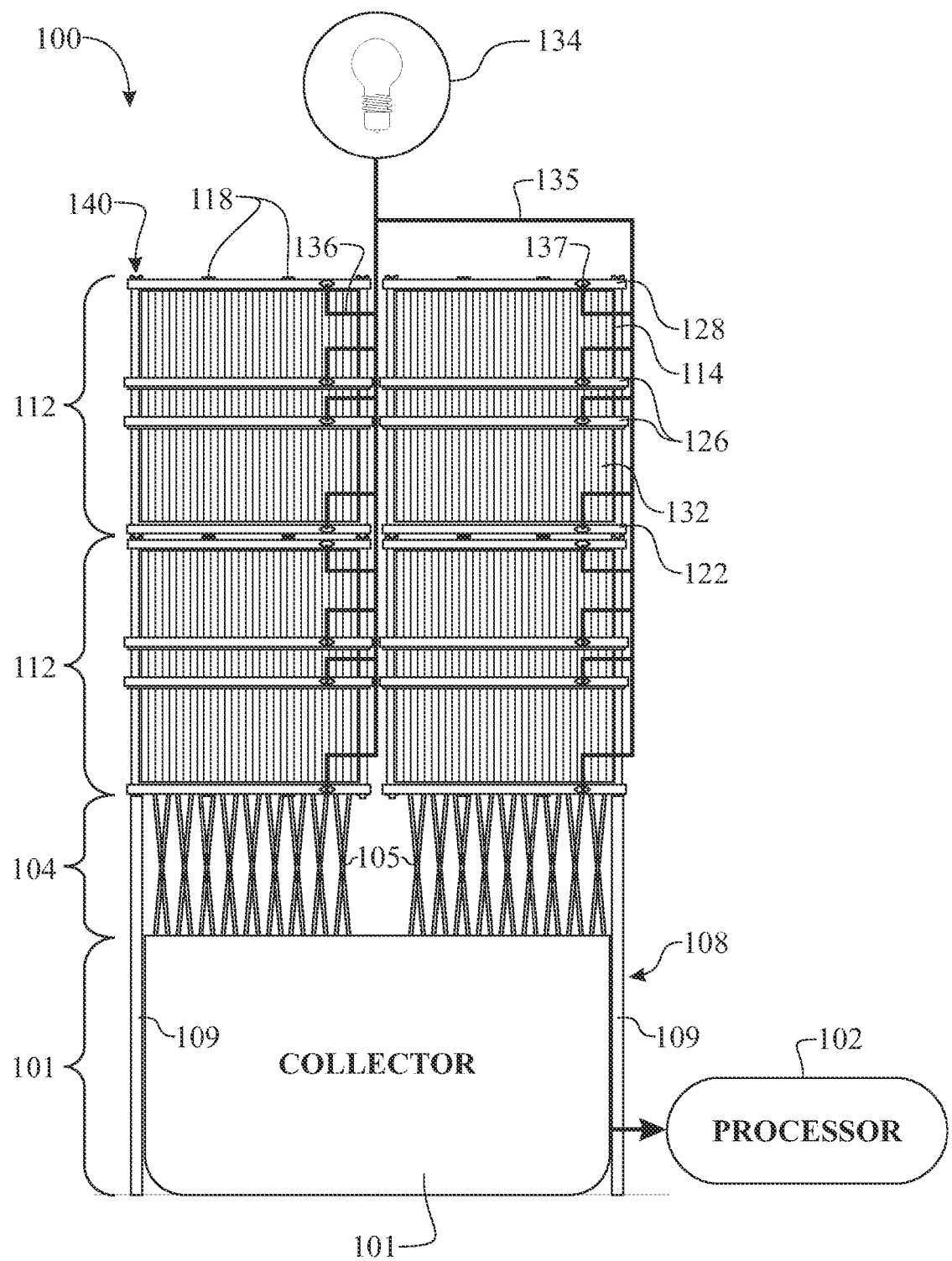
FIG. 1 is a partial schematic side view of an illustrative embodiment of the algae production and harvesting apparatus.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following.

Referring to the drawings, an illustrative embodiment of the algae production and harvesting apparatus (hereinafter "apparatus") is generally indicated by reference numeral 100 in FIGS. 1 and 2. The apparatus 100 may include at least one photobioreactor module 112, which is adapted to contain and sustain the growth of algae 133 (FIG. 8) as will be hereinafter further described. In some applications, multiple photobioreactor modules 112 may be stacked on top of each other to increase the algal growth capacity of the apparatus 100 without increasing its footprint. A collecting vessel (shown in FIG. 1 as a "Collector") 101 may be provided beneath the photobioreactor module or modules 112 to collect algal bioproducts (not illustrated) from algae 133 (FIG. 8) growing in the photobioreactor module or modules 112. The algal bioproducts can include any product of the algae 133 which may be used to produce algal fuel or other useful product. Algal bioproducts include, but are not limited to, algae, algae biomass, algae excretions and algae derivative products. A product processor 102 may communicate with the collecting vessel 101 to receive and process the algal bioproducts into algal fuel or other product. The product processor 102 may utilize conventional methods, which are known by those skilled in the art, to convert the algal bioproducts into algal fuel or other product. The product processor 102 may be a dryer, a press, a transesterfication processor, a refinement processor, a microwave processor or a sonic processor, for example and without limitation. Various processes may be employed to achieve the final desired product and the specific implementation for a particular product, as will be evident to one skilled in the art.

In some embodiments, a module support frame 108 may support the photobioreactor module(s) 112 over the collecting vessel 101. The module support frame 108 may include multiple vertical corner frame members 109, which support respective corners of the photobioreactor module(s) 112, and multiple center frame members 110 (indicated in phantom in FIG. 2), which support the center portion of the photobioreactor module(s) 112. In some embodiments, a product transfer assembly 104 may be interposed between the photobioreactor module(s) 112 and the collecting vessel 101, to facilitate drainage of algal bioproducts from the photobioreactor module(s) 112 into the collecting vessel 101, as will be hereinafter further described. The product transfer assembly 104 may include multiple product transfer tubes 105 extending from the photobioreactor module(s) 112 to the collecting vessel 101. Alternatively, product can be collected within plumbing connections of the array, and subsequently transmitted directly to the product processor 102.

Figure 7:
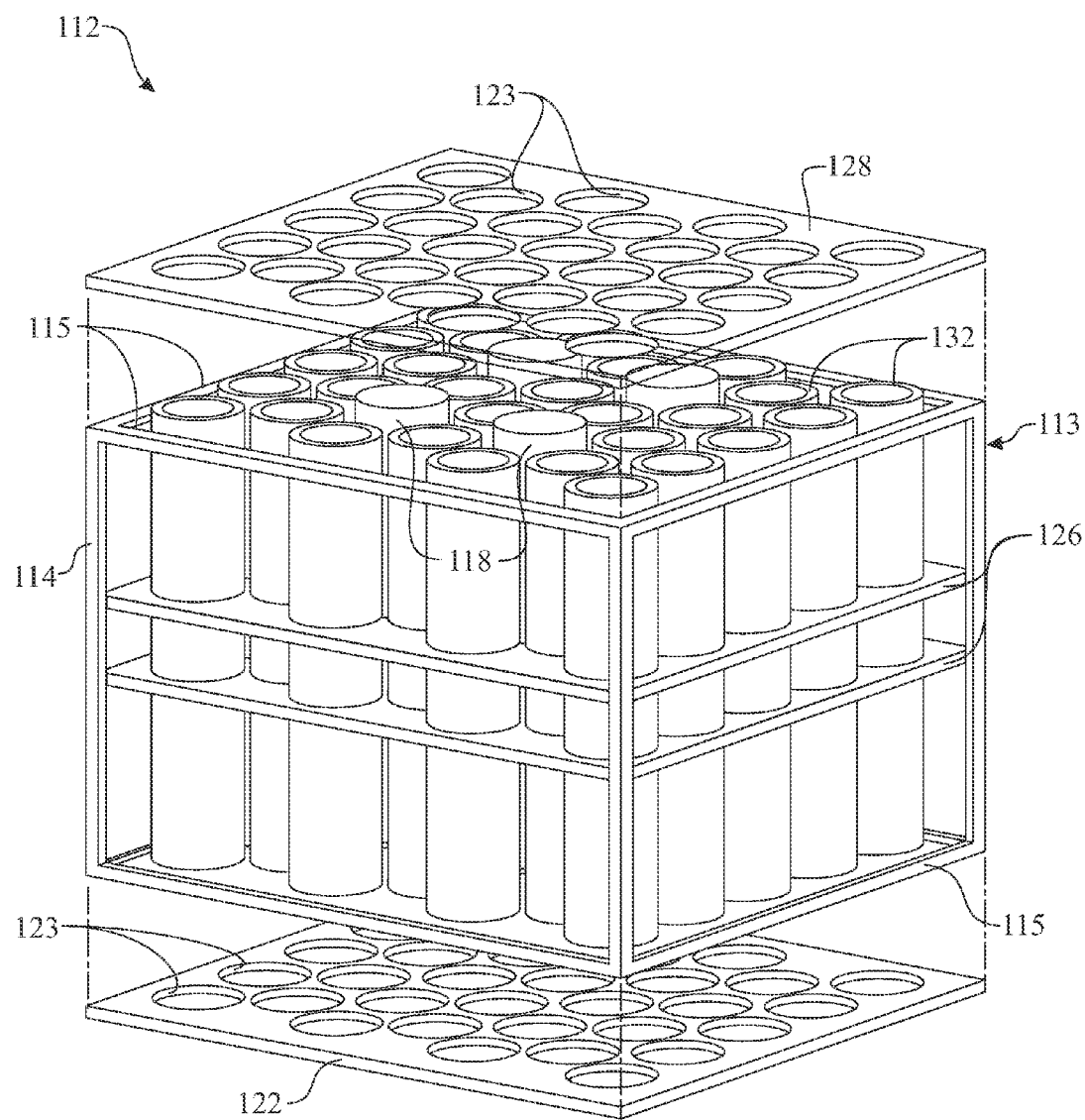
FIG. 7 is an exploded perspective view of a photobioreactor module of an illustrative embodiment of the algae production and harvesting apparatus.

As illustrated in FIG. 7, each photobioreactor module 112 of the apparatus 100 may include a module frame 113. At least one light-transmitting member 122, 126, 128 may be provided on the module frame 113. Each light-transmitting member 122, 126, 128 comprises a light transmitting material such as polycarbonate, for example and without limitation. Polycarbonate is well known to be highly transparent to visible light and has better light transmission characteristics than many kinds of glass. Multiple openings 123 for photobioreactor conduits 132 may be provided in each light-transmitting member 122, 126 and 128. An array of multiple photobioreactor conduits 132, each of which is a transparent and light-transmitting material, such as polycarbonate, for example and without limitation, may extend through the respective openings 123 of each light-transmitting panel 122, 126 and 128. Each opening 123 may correspond in shape and size to the cross-sectional configuration of each photobioreactor conduit 132. Accordingly, each photobioreactor conduit 132 is disposed in light-receiving relationship with respect to each light-transmitting panel 122, 126 and 128, along the surface area of contact between the photobioreactor conduit 132 and each light-transmitting member 122, 126 and 128, for purposes that will be hereinafter described. The light-transmitting characteristics of each photobioreactor conduit 132 may facilitate transmission of light that is received from the light-transmitting panels 122, 126 and 128, along substantially the entire length of the photobioreactor conduit 132. Each photobioreactor conduit 132 is adapted to contain algae 133 (FIG. 8) and may be geometrically shaped and configured to maximize exposure of the contained algae 133 to light, and to maximize internal distribution of the light throughout the photobioreactor conduit 132. It should be noted that the spacing of the openings 123 in the light-transmitting members 122, 128 is for illustrative purposes. As will be evident, one aspect of the apparatus is to provide conduits in an extremely dense arrangement. Accordingly, the exterior surfaces of adjacent conduit walls can be in physical contact with another. Furthermore, while the apparatus is illustrated in FIG. 7 as a plurality of individual conduits 132 extending through openings 123 in light transmitting members, this Disclosure contemplates the alternative fabrication of a unitary, or one-piece, module having a plurality of parallel linear channels extending through the unitary structure in such a manner that adjacent channels share a sidewall. In that case, each linear channel defines an interior channel space, which can be chosen having a pre-determined uniform cross-sectional area for maximizing growth of a particular algae strain. Such a one-piece module structure would replace the need for separate conduits 132 and light-transmitting members 122, 126 and 128, as well as the need for an external support structure.

Returning to the exemplary embodiment, the module frame 113 of each photobioreactor module 112 may have any design or structure that is suitable for supporting at least one light-transmitting member 122, 126, 128. As further illustrated in FIG. 7, in some embodiments the module frame 113 may have a generally cube-shaped configuration with four vertical corner supports 114, and a pair of upper and lower horizontal transverse supports 115 connecting the adjacent corner supports 114 to each other. In some embodiments, a bottom light-transmitting member 122 may be provided on the lower transverse supports 115 of the module frame 113. A top light-transmitting member 128 may be provided on the upper transverse supports 115. One or more spaced-apart middle light-transmitting member 126 may be provided in the module frame 113 between the bottom light-transmitting member 122 and the top light-transmitting member 128. Each photobioreactor conduit 132 may extend through aligned openings 123 provided in the bottom light-transmitting member 122, the middle light-transmitting member 126 and the top light-transmitting member 128, respectively. The bottom light-transmitting member 122, the middle light-transmitting member 126 and the top light-transmitting member 128, may be attached to the module frame 113 using adhesives, fasteners and/or any other suitable attachment technique known by those skilled in the art.

Figure 9:
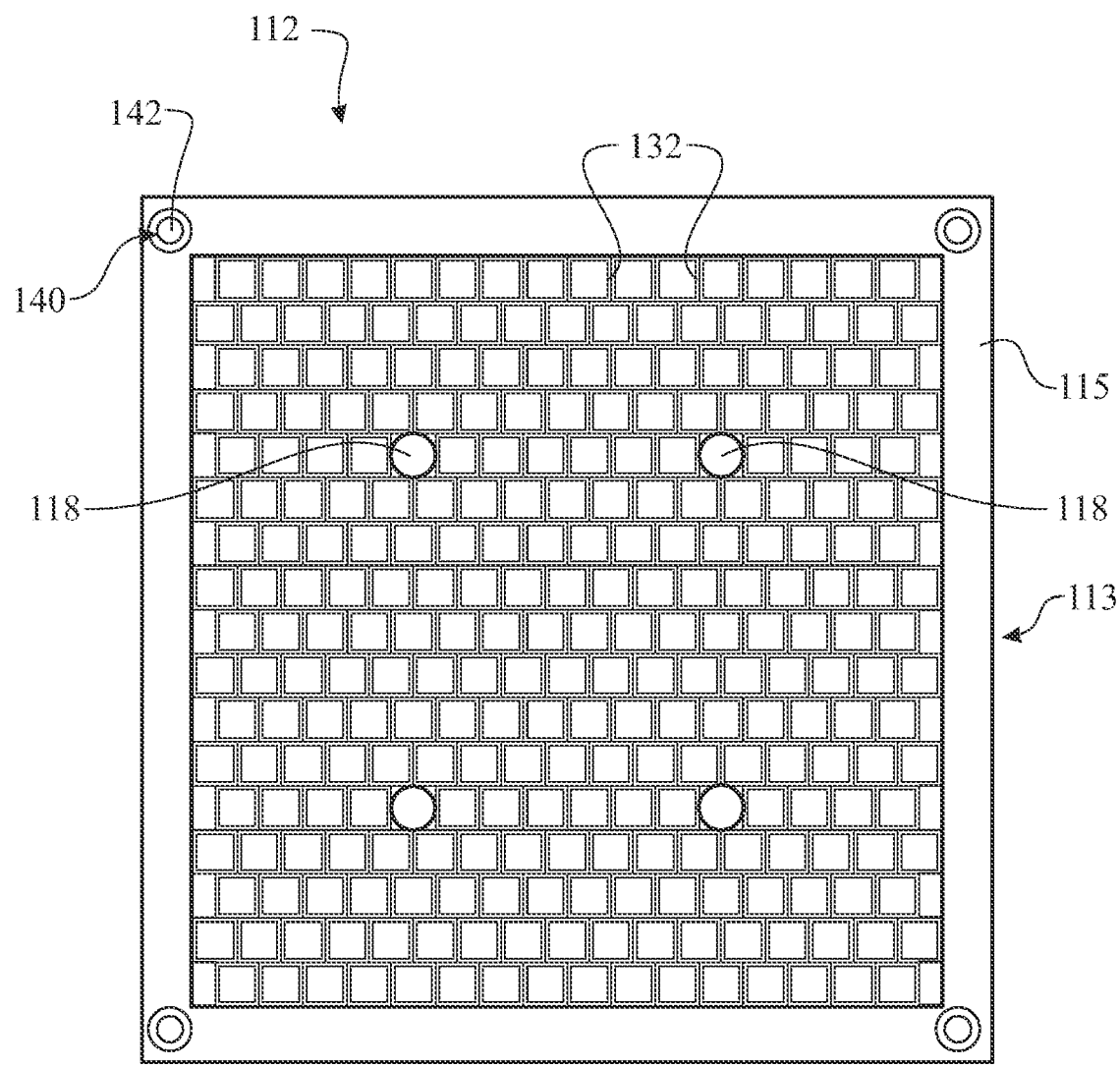
FIG. 9 is a top view of a photobioreactor module of an illustrative embodiment of the algae production and harvesting apparatus, in which the photobioreactor channels have a rectangular geometry.

As illustrated in FIG. 9, in some embodiments, at least one center plate support 118 may extend through center support openings (not illustrated) provided in each of the light-transmitting member 122, 126 and 128, for reinforcement. Each center plate support 118 may extend in generally parallel and adjacent relationship with respect to the photobioreactor conduits 132. In some embodiments, four center plate supports 118 may extend through the center support openings in the light-transmitting member 122, 126 and 128.

Figure 3:
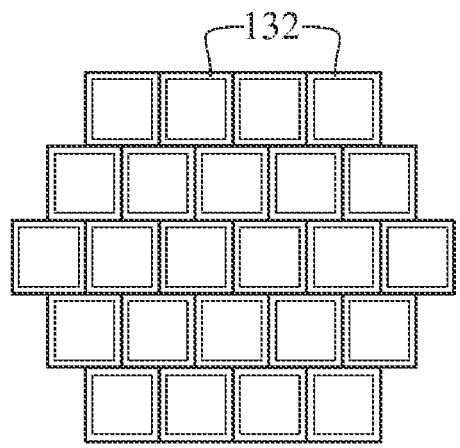
FIG. 3 is a top view of multiple photobioreactor conduits, or tubes, in a photobioreactor module of an illustrative embodiment of the algae production and harvesting apparatus, more particularly illustrating an exemplary rectangular photobioreactor channel geometry.
Figure 4:
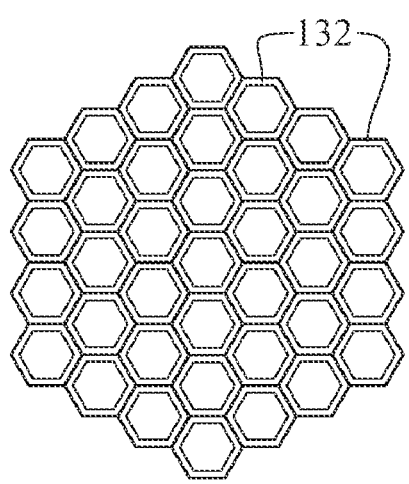
FIG. 4 is a top view of multiple photobioreactor channels, in a photobioreactor module of an illustrative embodiment of the algae production and harvesting apparatus, more particularly illustrating an exemplary hexagonal photobioreactor channel geometry.
Figure 5:
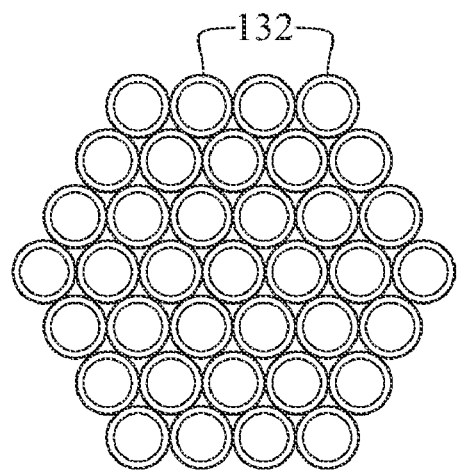
FIG. 5 is a top view of multiple photobioreactor channels, in a photobioreactor module of an illustrative embodiment of the algae production and harvesting apparatus, more particularly illustrating an exemplary circular photobioreactor channel geometry.
Figure 8:
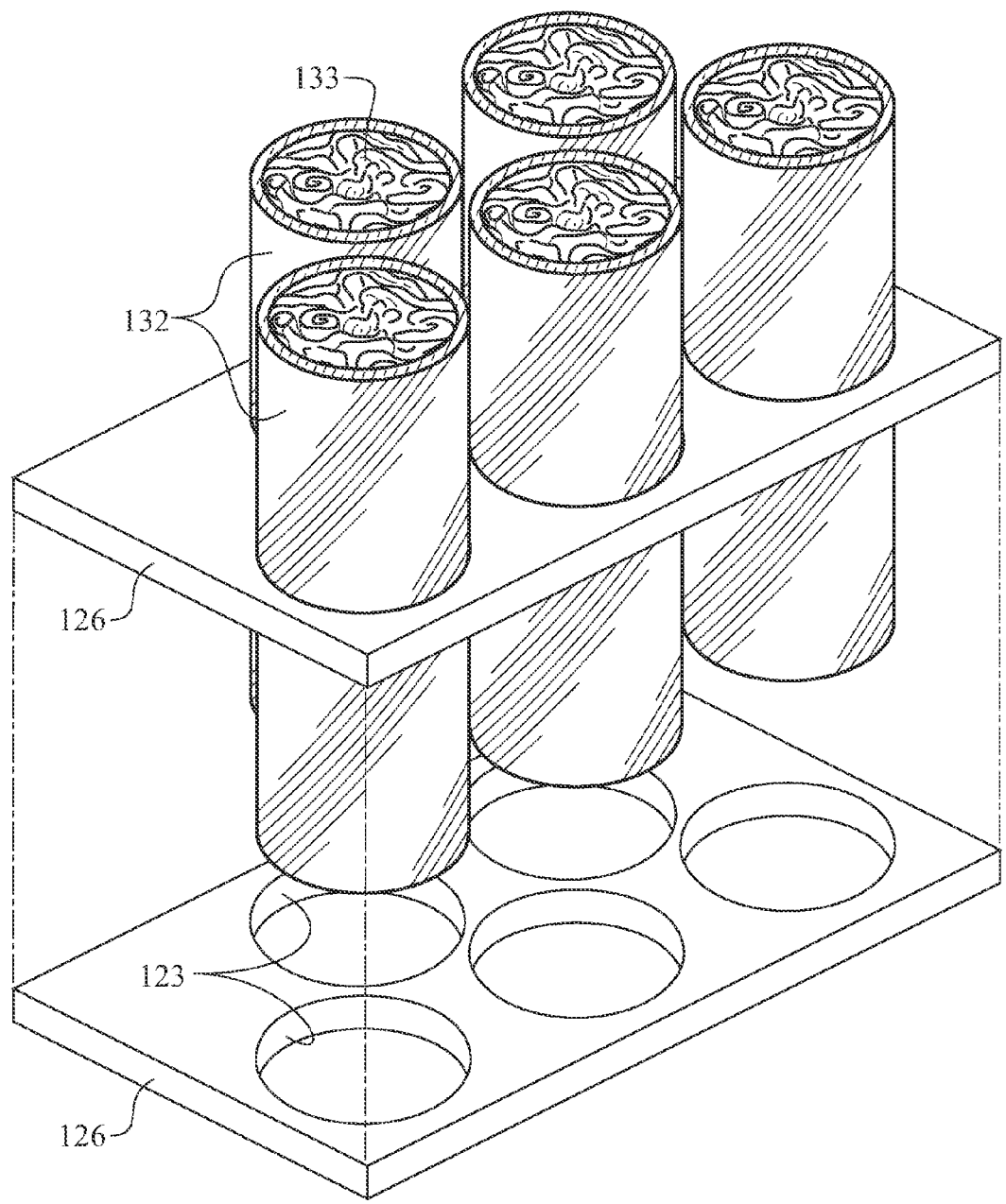
FIG. 8 is a perspective view of multiple photobioreactor channels extending through light-transmitting module panels.

The photobioreactor conduits 132 of each photobioreactor module 112 may have any desired cross-sectional configuration. As illustrated in FIG. 3, in some embodiments each photobioreactor conduit 132 may have a generally rectangular cross-section. As illustrated in FIG. 4, in some embodiments each photobioreactor conduit 132 may have a generally hexagonal cross-section. As illustrated in FIG. 5, in some embodiments each photobioreactor conduit 132 may have a generally circular cross-section. Other cross-sectional geometries, such as triangular, pentagonal and octagonal, for example and without limitation, are possible. As illustrated in FIG. 8, in implementation of the apparatus 100, which will be hereinafter described, algae 133 may be grown in each photobioreactor conduit 132 for the purpose of harvesting algal bioproducts (not illustrated) from the algae 133. The particular cross-sectional geometry, and cross-sectional area, of each photobioreactor conduit 132 may depend upon such factors as the characteristics of the particular strain of algae 133 being grown in the algae growth conduits 132, the range of environmental parameters required by any specific strain of algae for maximization of photosynthetic efficiency, variable exposure requirements to various light sources and spectrum, intensity of exposure, containment volume and the specific manufacturing methods used to fabricate the algae growth conduits 132.

Figure 2:
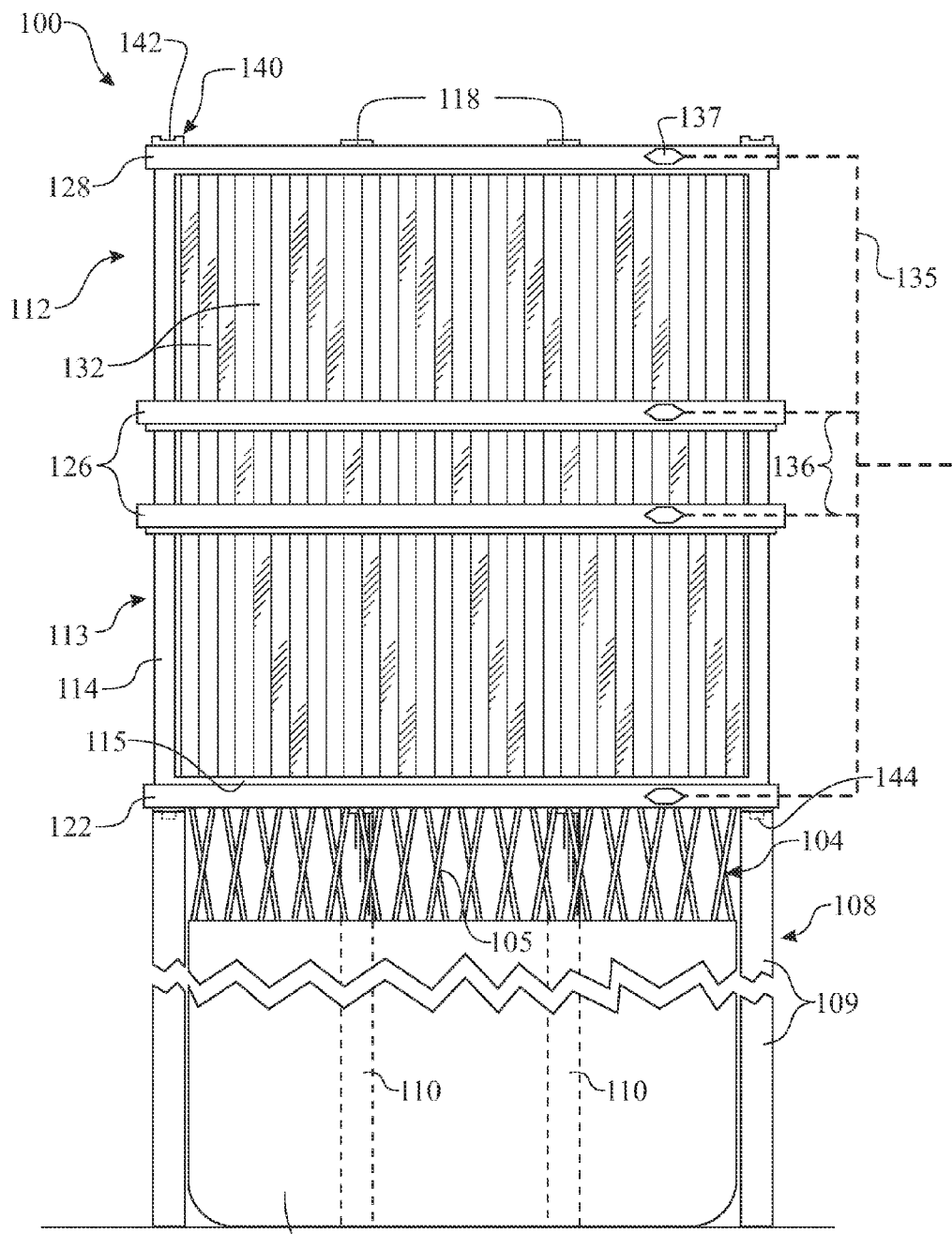
FIG. 2 is a side view of an illustrative embodiment of the algae production and harvesting apparatus, with a collecting vessel provided beneath a photobioreactor module, and a product transfer assembly provided in fluid communication between the photobioreactor module and the collecting vessel.

As illustrated in FIGS. 1 and 2 of the drawings, a light source 134 shown as a light bulb (only for example) may be disposed in optical communication with each of the light-transmitting member 122, 126 and 128. In some embodiments, fiber optic light transmission cables 135 may be disposed in optical communication with the light source 134. Light tubing branches 136 may branch from each light transmission cable 135. A light-transmitting connection terminal 137 may be used to connect light transmission cable branches 136 to the light transmitting members 122, 126 and 128. The light source 134 can be natural light, artificial light, or a combination of both natural light and artificial light. Each light-transmitting member 122, 126 and 128 imparts structural rigidity to the photobioreactor module 112, and provides a medium for transfer of light from the light source 134 to the photobioreactor conduits 132.

Figure 6:
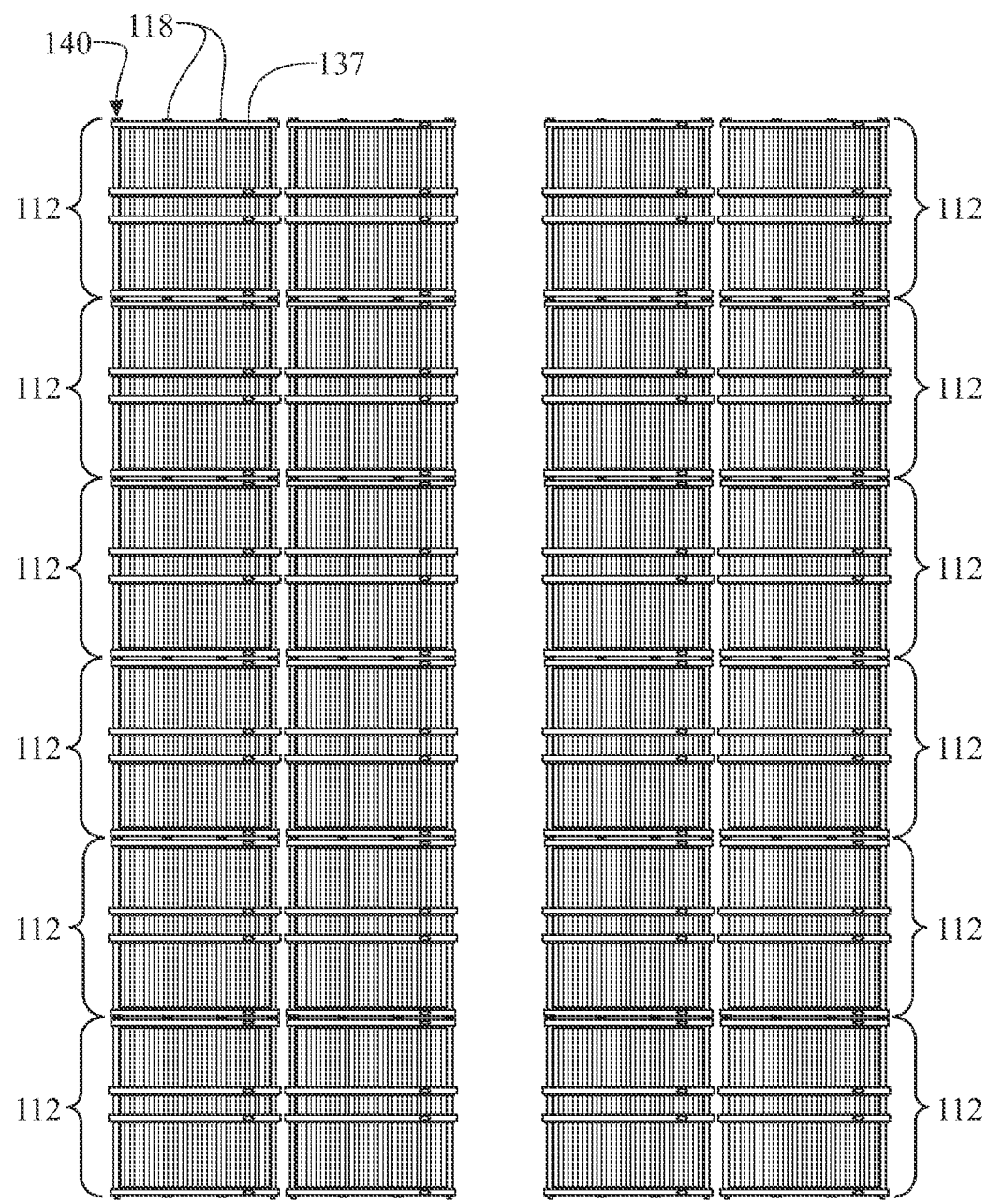
FIG. 6 is a side view of multiple stacked photobioreactor modules in implementation of an illustrative embodiment of the algae production and harvesting apparatus.
Figure 10:
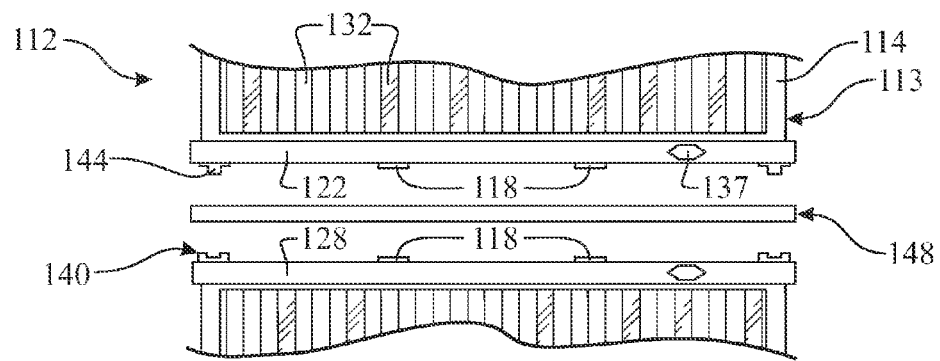
FIG. 10 is an exploded view, partially in section, of a pair of stacked photobioreactor modules, illustrating a gasket interposed between the photobioreactor modules.
Figure 11:
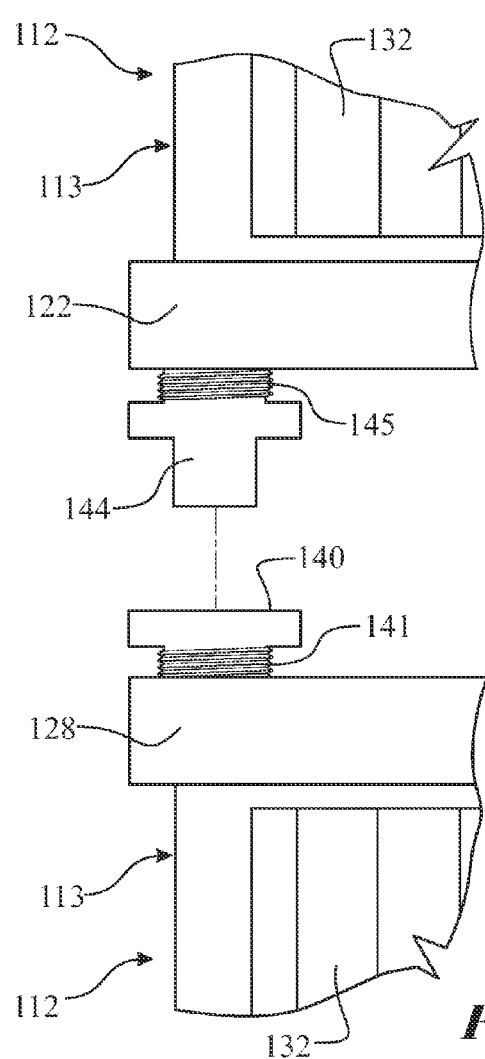
FIG. 11 is a sectional view of a pair of stacked photobioreactor modules, more particularly illustrating an exemplary manner of securing the upper photobioreactor module on the lower photobioreactor module by seating a module foot provided on the upper photobioreactor module in a module receptacle provided on the lower photobioreactor module.
Figure 12:
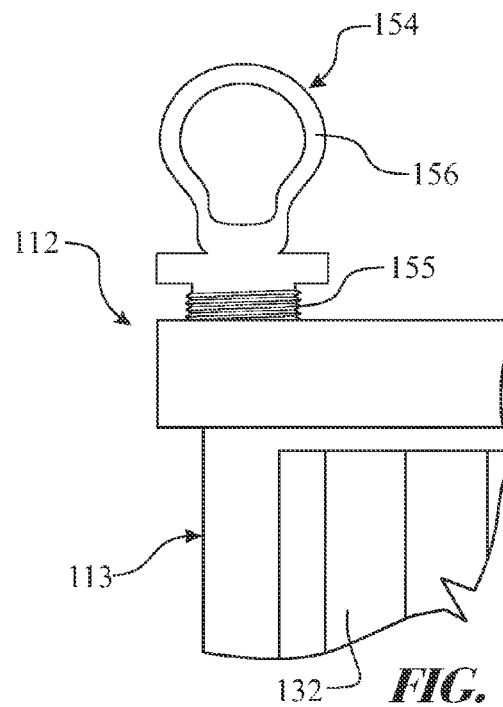
FIG. 12 is a sectional view of an upper corner of an photobioreactor module, with a module lifting shackle (or lift plug) threaded into a module receptacle opening (not illustrated) provided in the uppermost photobioreactor module of the algae production and harvesting apparatus in place of a module receptacle.

As illustrated in FIGS. 1 and 6 of the drawings, in some applications of the apparatus 100, multiple photobioreactor modules 112 may be stacked on top of each other to selectively increase the algal growth capacity of the apparatus 100. The stacked photobioreactor modules 112 may be stabilized on top of each other according to any suitable technique, as known by those skilled in the art. For example, as illustrated in FIGS. 10-12, in some embodiments multiple module receptacles 140, each having a receptacle seat 142 (FIG. 9), may be provided at respective corners of the top light-transmitting member 128 of each photobioreactor module 112. Each module receptacle 140 may be fitted with multiple receptacle threads 141 to facilitate threaded insertion of each module receptacle 140 into a corresponding receptacle opening in the corresponding module frame (not illustrated) provided through the top light-transmitting panel 128. Multiple module frame feet 144 may be provided, at respective corners, through the bottom light-transmitting member 122 of each photobioreactor module 112. Each module foot 144 may be fitted with multiple foot threads 145 to facilitate threaded insertion of each module foot 144 into a corresponding foot opening (not illustrated) provided through the bottom light-transmitting member 122. Accordingly, as illustrated in FIG. 11, the module feet 144 of an upper photobioreactor module 112 may be seated in the receptacle seats 142 (FIG. 9) of the respective module receptacles 140, to stabilize the upper photobioreactor module 112 on the lower photobioreactor module 112. As illustrated in FIG. 6, it will be appreciated by those skilled in the art that any number of photobioreactor modules 112 may be stacked in the apparatus 100 to correspondingly increase the algae growing capacity of the apparatus 100. Moreover, multiple apparatus 100, each having multiple stacked photobioreactor modules 112, may be provided in adjacent relationship to increase algae growth capacity while minimizing footprint space occupied by the apparatus 100.

As illustrated in FIG. 12, in some embodiments a module lifting shackle 154 may be inserted into each module receptacle opening (not illustrated) provided through the top light-transmitting panel 128 of the uppermost photobioreactor module 112 in the apparatus 100. Each module lifting shackle 154 may include threads 155 and a loop 156. A cable (not illustrated) provided on a hoisting apparatus (not illustrated) may be fastened to the shackle loop 156 of each module lifting shackle 154, to facilitate selective raising and lowering of the uppermost photobioreactor module 112, with respect to the immediately underlying photobioreactor module 112 of the stack, by operation of the hoisting apparatus.

Figure 15:
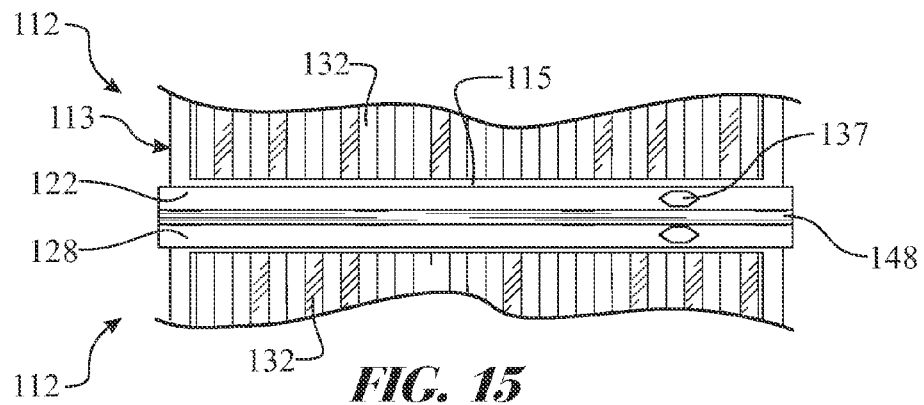
FIG. 15 is a sectional view of a pair of stacked photobioreactor modules having a gasket interposed between the modules.
Figure 16:
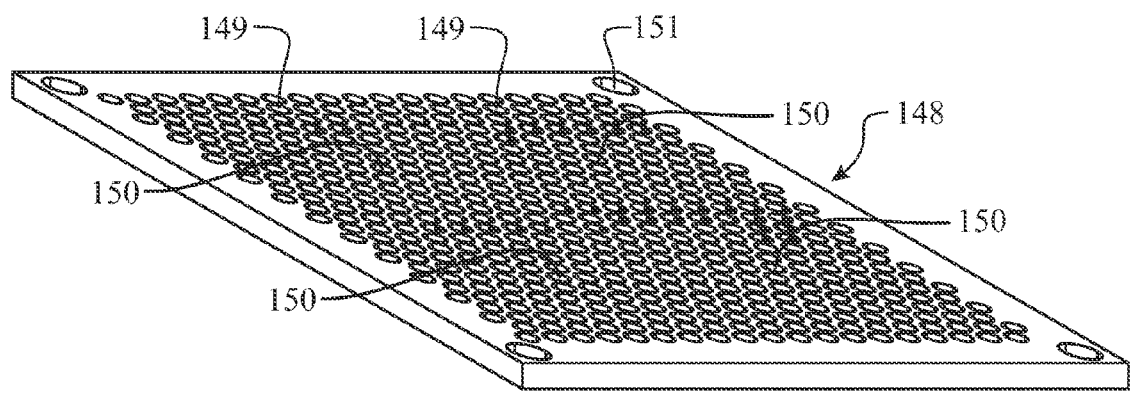
FIG. 16 is a perspective view of an illustrative gasket for providing sealing between the stacked photobioreactor modules.

As illustrated in FIGS. 10, 15 and 16, in some embodiments, a gasket 148 may be interposed between the top light-transmitting member 128 of each photobioreactor module 112 and the bottom light-transmitting member 122 of the next highest photobioreactor module 112 in the stack. As illustrated in FIG. 16, each gasket 148 may include multiple conduit openings 149, which establish fluid communication between the photobioreactor conduits 132 of the respective stacked photobioreactor modules 112. In some embodiments, at least one center support opening 150 may be provided in the center portion of the gasket 148, to accommodate the end of at least one of the center plate supports 118. Corner openings 151 may be provided at the respective corners of each gasket 148, to accommodate the module receptacles 140 on the lower photobioreactor module 112 and the module feet 144 on the upper photobioreactor module 112. Accordingly, the gasket 148 may provide a fluid-tight seal between the photobioreactor conduits 132 of adjacent photobioreactor modules 112.

Figure 13:
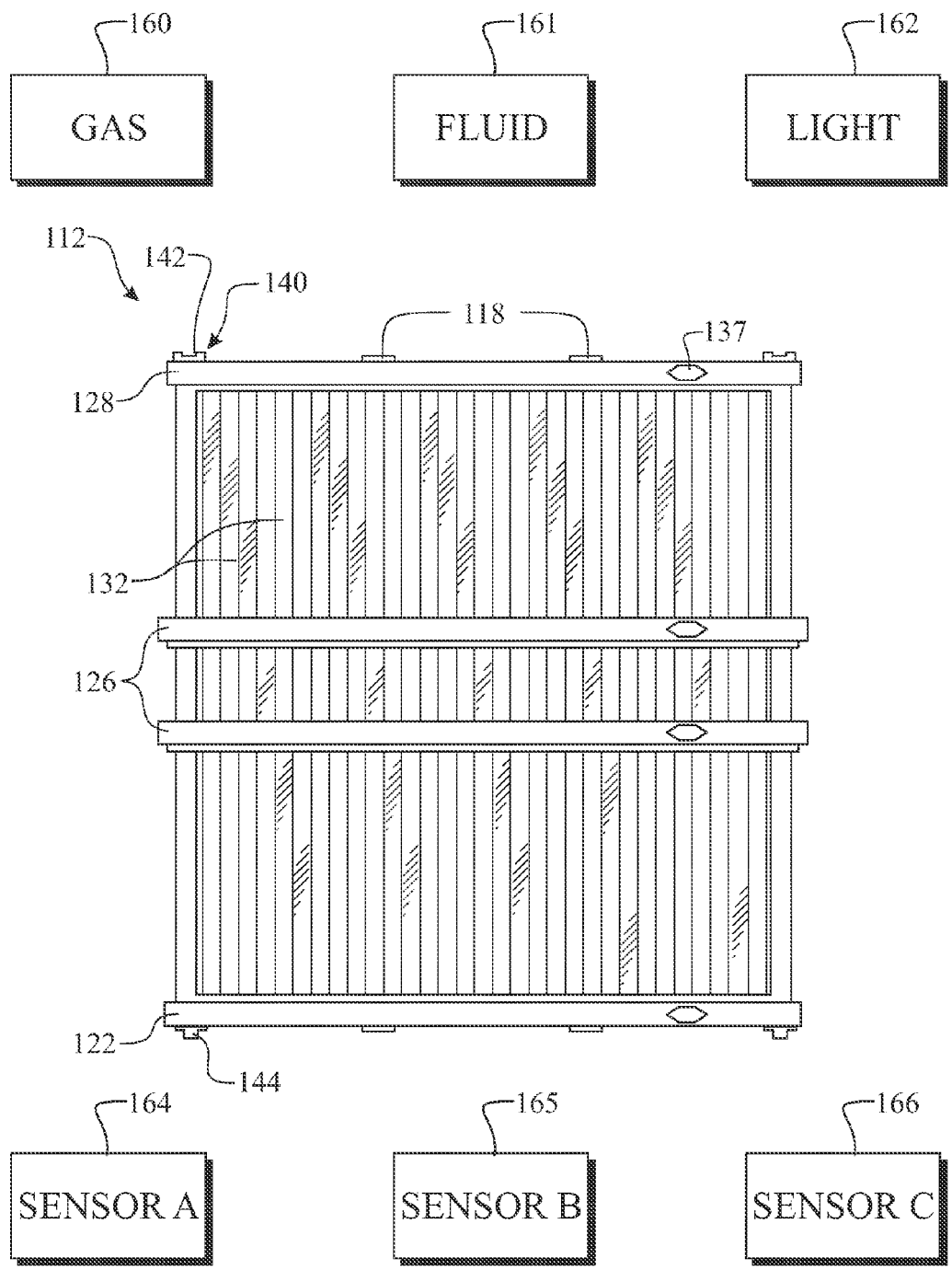
FIG. 13 is a schematic diagram which illustrates inclusion of sensors for gas, fluid and light, respectively, in a photobioreactor module of an illustrative embodiment of the algae production and harvesting apparatus.
Figure 14:
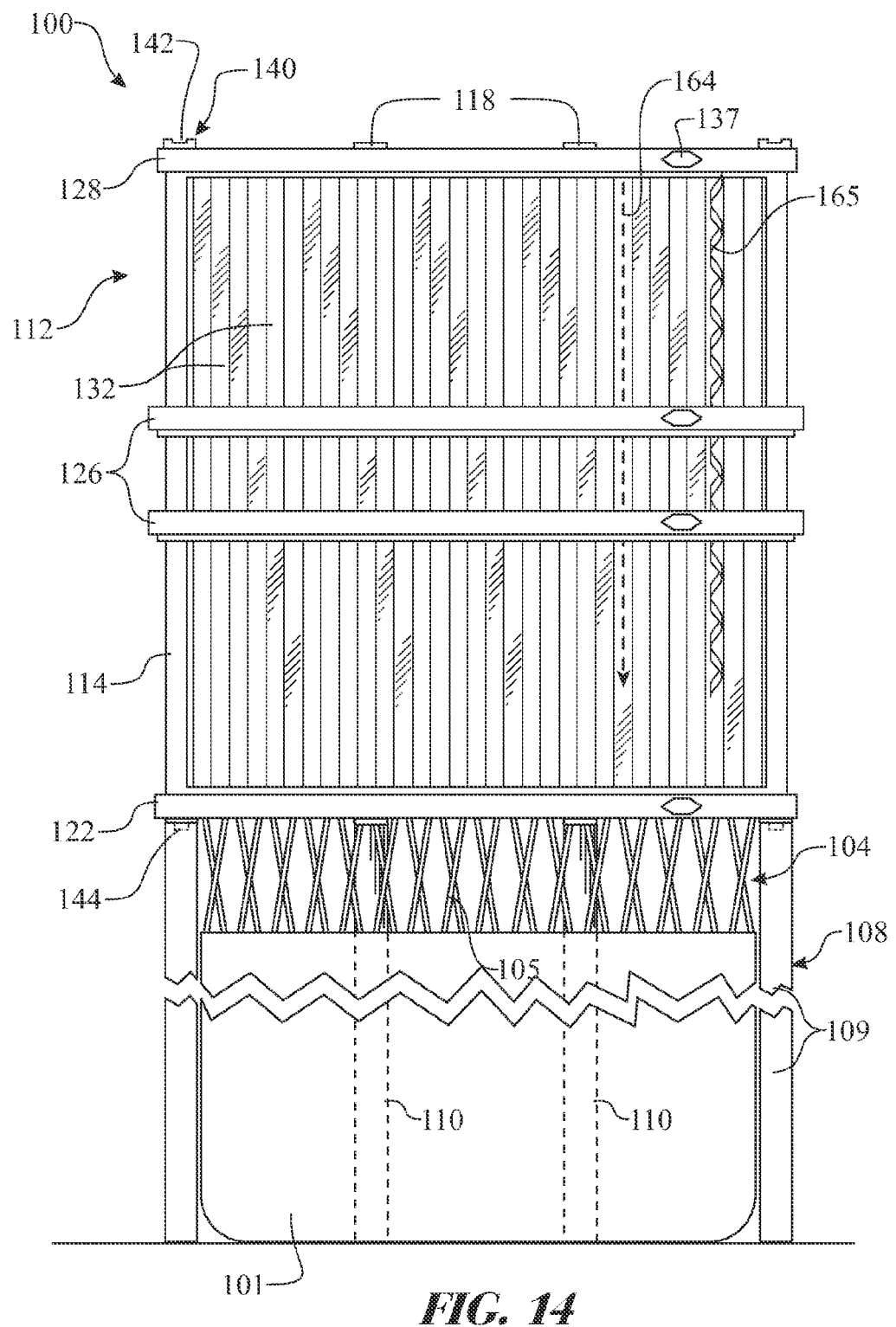
FIG. 14 is a side view of an illustrative embodiment of the algae production and harvesting apparatus, with a pair of sensors provided in a pair of photobioreactor tubes, respectively, in a photobioreactor module of the algae bioproduct harvesting apparatus.

In addition to facilitating the control of light- and temperature-related factors, disclosed apparatus allows for the control of other elements affecting the rate of growth of the algae, such as $CO_2$ concentration, $O_2$ levels, and nutrient levels. As illustrated in FIG. 13 of the drawings, gas 160, fluid 161, light 162 and other substances or elements, may be provided as required for sustenance and growth of the algae 133 in each of the photobioreactor conduits 132 of each photobioreactor module 112. As described above, tThe light 162 may be natural light, artificial light or a combination thereof, provided by the light source 134 (FIG. 1). The gas 160, fluid 161, and other elements required for sustenance and growth of the algae 133 may be provided in a growth medium (not illustrated) in which the algae 133 are suspended in each photobioreactor conduit 132. In some embodiments, each photobioreactor module 112 may include sensors (which are designated schematically as "SENSOR A," "SENSOR B" and "SENSOR C," in FIG. 13) adapted to sense various parameters of the gas 160, fluid 161, light 162, or other substances or elements required for sustenance and growth of the algae 133. For example, in FIG. 13, SENSOR A may be a gas sensor 164 that senses the presence, concentration and/or other parameters, of an algae-sustaining gas 160 in the photobioreactor conduits 132; SENSOR B may be a fluid sensor 165 that senses the presence, quantity and/or other parameters, of a fluid 161 in the photobioreactor conduits 132; and SENSOR C may be a light sensor 166 that senses the presence, spectrum and/or other parameters, of light 162 to which the algae 133 is exposed. The gas sensor 164, the fluid sensor 165 and/or the light sensor 166, may be adapted to determine the permissible ranges of concentrations or quantities of the gas 160, the fluid 161 and/or other substances or elements, and the spectrum, intensity, source and destination within the apparatus 100, of the light 162, to facilitate changes to the concentrations, quantities and other parameters, in order to ensure optimum growth of the algae 133 in the photobioreactor conduits 132. As illustrated in FIG. 14, the gas sensor 164, the fluid sensor 165, the light sensor 166 (FIG. 13) and any additional sensors, may be provided in one or more of the photobioreactor conduits 132 of each photobioreactor module 112. Carbon molecules, growth medium and other substances that may be necessary for sustenance and growth of the algae 133, may be supplied to the algae 133 by various processes, including, but not limited to, an atmospheric or environmental scrubber, compressed concentrate and industrial emissions. In some embodiments, a coolant (not illustrated) may be provided in each photobioreactor conduit 132 to assist in control of internal environmental temperatures.

Figure 17:
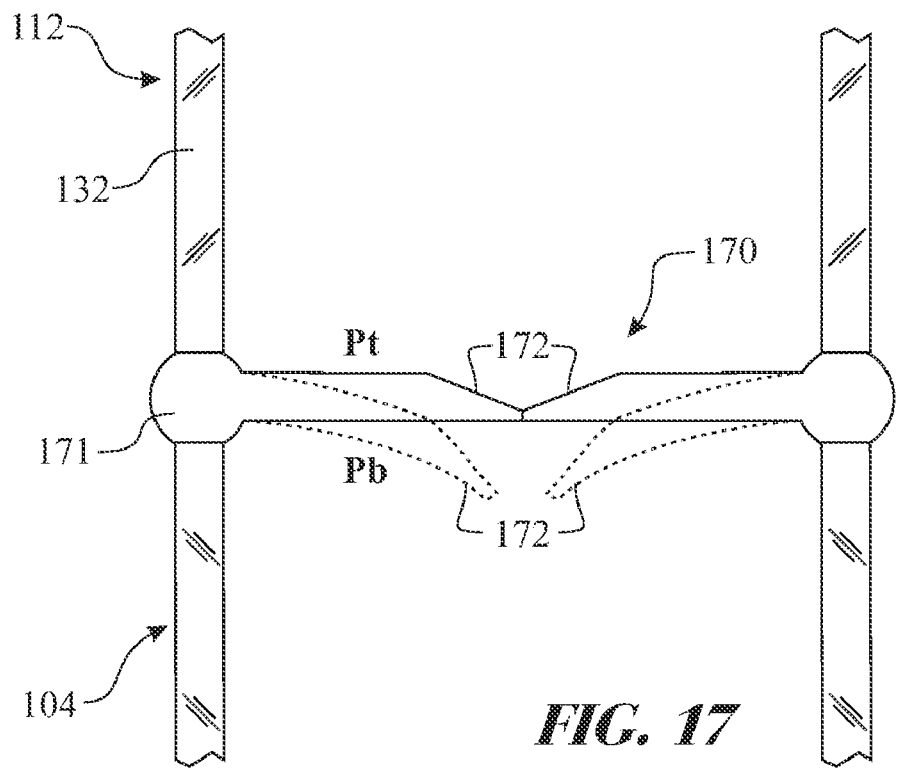
FIG. 17 is a sectional view of an exemplary flow control device for controlling flow of algae product from each photobioreactor channel into the product transfer assembly.
Figure 18:
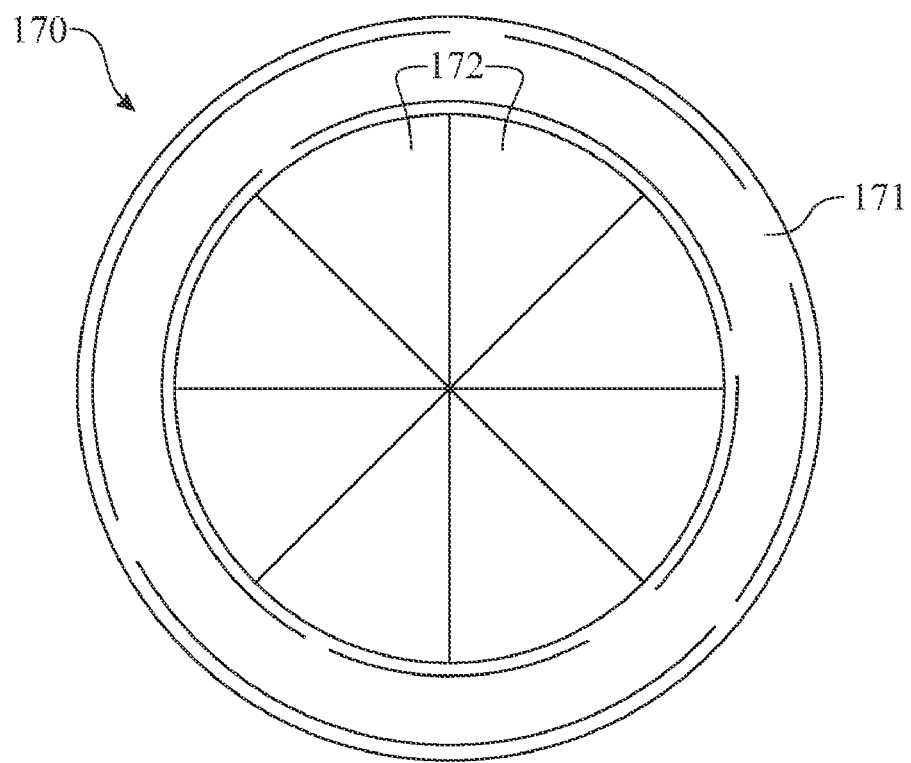
FIG. 18 is a top view of the exemplary flow control device illustrated in FIG. 17.

As illustrated in FIGS. 17 and 18 of the drawings, in some embodiments a flow control device 170 may be provided in each photobioreactor conduit 132 to retain algae 133 therein while enabling algal bioproducts (not illustrated) to flow under the influence of gravity from each photobioreactor conduit 132 and into the respective product transfer tubes 105 of the product transfer assembly 104. The flow control device 170 may include a device rim 171, which is attached to the photobioreactor conduit 132 according to the knowledge of those skilled in the art. Multiple, flexible device flaps 172 may extend inwardly from the device rim 171. A vacuum pump (not illustrated) may be disposed in communication with the product transfer tubes 105 of the product transfer assembly 104. Accordingly, upon application of reduced pressure to each photobioreactor conduit 132 via actuation of the vacuum pump, the device flaps 172 may be deflected from the closed, planar configuration (indicated by the solid lines in FIG. 17), to the downwardly extending configuration (indicated by the phantom lines in FIG. 17). Therefore, algal bioproducts (not illustrated) may be drawn from the photobioreactor conduits 132, through the downwardly-deflected device flaps 172 of the flow control device 170, and into the respective product transfer tubes 105 of the product transfer assembly 104.

In typical application, the apparatus 100 may be used to produce and harvest algal bioproducts (not illustrated) such as algae biomass, algae excretions, and algae derivative products, for example and without limitation. The algal bioproducts may be used to produce algal fuel or other useful product. Accordingly, as illustrated in FIG. 8, algae 133 may be placed in each of the photobioreactor conduits 132 of each photobioreactor module 112. The algae 133 may be suspended in an algal growth medium (not illustrated) containing the gases 160 and fluids 161 (FIG. 13) and any other chemicals, substances and nutrients, that may be necessary for sustenance and growth of the algae 133. The interior of the photobioreactor conduits 132 may be accessed through the respective openings 123 (FIG. 7) provided in the top light-transmitting panel 128 of the photobioreactor module 112. Depending upon the production requirements of the algal bioproducts to be harvested from algae 133, a selected number of the photobioreactor modules 112 may be stacked on top of each other, for example, in the manner that was heretofore described with respect to FIGS. 10 and 11. Moreover, as illustrated in FIG. 6, multiple apparatus 100 each having a selected number of stacked photobioreactor modules 112, may be placed in generally adjacent relationship with respect to each other, to further increase the algal growth capacity of the apparatus 100.

The light source 134 (FIG. 1) may be operated to transmit light 162 (FIG. 13) into each photobioreactor conduit 132 of each photobioreactor module 112 through the light transmission cables 135, the light tubing branches 136 and the light-transmitting members 122, 126 and 128, respectively. The light 162 is transmitted from each light-transmitting member 122, 126 and 128, into each photobioreactor conduit 132, at the contact surfaces between the light-transmitting member 122, 126 and 128, and each corresponding photobioreactor conduit 132. Accordingly, the algae 133 are sustained by gases 160, fluids 161, light 162, and nutrients and substances disposed in the growth medium inside each photobioreactor conduit 132. The gas sensor 164, the fluid sensor 165, the light sensor 166 (FIG. 13) and any additional sensors (not illustrated), may indicate the ranges of various parameters of the gas 160, fluid 161, light 162, and other substances to which the algae 133 are exposed in each photobioreactor conduit 132. The types and quantities of gas 160, fluid 161, light 162 and other substances may be adjusted to maintain those elements within the ranges for optimum sustenance and growth of the algae 133 in the photobioreactor conduits 132.

As a result of their growth and metabolism, the algae 133 produce algal bioproducts (not illustrated), which may include, but are not limited to, algae biomass, algae excretions and algae derivative products. The algal bioproducts which are produced by the algae 133 may drain from the photobioreactor conduits 132 of each photobioreactor module 112, through the product transfer tubes 105 of the product transfer assembly 104, into the collecting vessel 101 of the apparatus 100. In some embodiments, a vacuum pump (not illustrated) may be operated to draw the algal bioproducts from each photobioreactor conduit 132, through the product transfer tubes 105 of the product transfer assembly 104, into the collecting vessel 101. The algal bioproducts may then be pumped, transported, dropped or otherwise moved, from the collecting vessel 101 into the product processor 102. The product processor 102 may transform the algal bioproducts into algal fuel or other product. In applications in which multiple photobioreactor modules 112 are stacked on the product transfer assembly 104 of the apparatus 100, the gasket 148 (FIGS. 10, 15 and 16) is interposed between the photobioreactor modules 112 provides a fluid-tight seal between the photobioreactor conduits 132 of the respective photobioreactor modules 112. Photobioreactor modules 112 may be selectively removed from, or added to, the apparatus 100 by attaching the module lift plugs 154 (FIG. 12) to the top light-transmitting panel 128 of each added or removed photobioreactor module 112, in lieu of the module receptacles 140 (FIG. 11), and extending a cable (not illustrated) attached to a hoisting apparatus (not illustrated) through the plug loop 156 of each module lift plug 154. The hoisting apparatus may then be operated to lift the uppermost photobioreactor module 112 from the apparatus 100, or to lower an additional photobioreactor module 112 onto the uppermost photobioreactor module 112 of the apparatus 100.

Since many modifications, variations, and changes in detail can be made to the described embodiments herein, it is intended that all matters in the foregoing description and shown in the accompanying drawings be interpreted as illustrative and not in a limiting sense. Thus, the scope of this Disclosure should be determined by the appended claims and their legal equivalence. By way of example, although not shown in the exemplary embodiments, alternative conduit arrangements, such as the incorporation of concentrically arranged conduits, is contemplated. Furthermore, while the exemplary embodiments described and depicted herein detail the withdrawal, or harvesting, of algal material from the bottom of the module, it will be apparent to those skilled in the art that algal material could just as easily be harvested from the top of the modules via installation of, for example, collector tubes and manifold devices.

What is claimed is:

1. A photo-bioreactor module for producing algal bioproducts, comprising:
    at least an upper and a lower light-transmitting member each having a plurality of openings, wherein said upper and said lower light-transmitting members are spaced apart from one another and at least one of said upper and said lower light-transmitting members includes at least one light connection terminal for coupling in light from a light source and transmitting said light laterally, and
    a plurality of photobioreactor conduits each extending from respective openings in said upper and said lower light-transmitting member and defining an algae containment interior space, wherein said plurality of photobioreactor conduits contact said upper and a lower light-transmitting members along areas of contact,
    wherein said light transmitted laterally by said upper and said lower light-transmitting members couples into said plurality of photobioreactor conduits along said areas of contact.

2. The photo-bioreactor module of claim 1, further comprising at least one solid support extending from between respective ones of said plurality of openings in said upper and a lower light-transmitting member for structural reinforcement.

3. The photo-bioreactor module of claim 1, wherein said plurality of photobioreactor conduits share sidewalls.

4. The photo-bioreactor module of claim 3, wherein said photo-bioreactor module is a one piece (unitary) structure.

5. The photo-bioreactor module of claim 1, wherein said plurality of photobioreactor conduits each have their own sidewalls, wherein adjacent surfaces of said sidewalls are in physical contact.

6. The photo-bioreactor module of claim 1, wherein said light connection terminal is configured for receiving a light transmission cable.

7. The photo-bioreactor module of claim 1, further comprising at least one of a gas sensor, a fluid sensor, a temperature sensor and a light sensor in at least one of said photo-bioreactor conduits.

8. The photo-bioreactor module of claim 1, further comprising at least one additional light-transmitting member interposed between said an upper and said lower light-transmitting member.

9. The photo-bioreactor module of claim 1, wherein said lower and said upper light-transmitting member and said plurality of photobioreactor conduits both comprise polycarbonate.

10. A vertically stacked modular apparatus for algae production and harvesting, comprising:
    a plurality of photo-bioreactor modules stacked on top of each other for producing algal bioproducts, said photobioreactor modules each comprising:
        at least an upper and a lower light-transmitting member each having a plurality of openings, wherein said upper and said lower light-transmitting members are spaced apart from one another and at least one of said upper and said lower light-transmitting members includes at least one light connection terminal for coupling in light from a light source and transmitting said light laterally, and
        a plurality of photobioreactor conduits each extending from respective openings in said upper and said lower light-transmitting member and defining an algae containment interior space, wherein said plurality of photobioreactor conduits contact said upper and a lower light-transmitting members along areas of contact,
        wherein said light transmitted laterally by said upper and said lower light-transmitting members couples into said plurality of photobioreactor conduits along said areas of contact, and
        a gasket comprising a plurality of conduit openings interposed between adjacent ones of said plurality of photo-bioreactor modules for providing a fluid-tight seal for module-to module fluid communication between respective ones of said plurality of photobioreactor conduits that are stacked on top of one another.

11. The vertically stacked modular apparatus of claim 10, wherein said plurality of photo-bioreactor modules further comprise threaded receptacles disposed on corners on one side said plurality of said photo-bioreactor modules and threaded module feet on corners of the other side of said plurality of photo-bioreactor modules, and wherein said threaded module feet from an upper one of said plurality of photo-bioreactor modules is threadably inserted into said threaded receptacles of a lower one of said plurality of photo-bioreactor modules.

12. The vertically stacked modular apparatus of claim 10, wherein each of said plurality of photo-bioreactor modules further comprise at least one solid support extending from between respective openings in said upper and a lower light-transmitting member for structural reinforcement.

13. The vertically stacked modular apparatus of claim 10, wherein said plurality of photobioreactor conduits in each of said plurality of photo-bioreactor modules share sidewalls.

14. The vertically stacked modular apparatus of claim 13, wherein said plurality of photo-bioreactor modules are each one piece (unitary) structures.

15. The vertically stacked modular apparatus of claim 10, wherein said plurality of photobioreactor conduits in each of said plurality of photo-bioreactor modules each have their own sidewalls, wherein adjacent surfaces of said sidewalls are in physical contact.

16. The vertically stacked modular apparatus of claim 10, wherein said light connection terminals in each of said plurality of photo-bioreactor modules are configured for receiving a light transmission cable.

17. The vertically stacked modular apparatus of claim 10, further comprising fiber optic light transmission cables coupled to said light connection terminals for transmitting said light from said light source into each of said upper and said lower light-transmitting members.

18. The vertically stacked modular apparatus of claim 10, further comprising at least one additional light-transmitting member interposed between said upper and said lower light-transmitting member.

19. A method for producing algal bioproducts, comprising:
   providing algae in at least one bioreactor module comprising a plurality of photobioreactor conduits that each define an algae containment interior space each extending from respective openings in an upper and a lower light-transmitting member, wherein said plurality of photobioreactor conduits contact said upper and said lower light-transmitting members along areas of contact,
   laterally transmitting light that is received by said upper and said lower light-transmitting member to said plurality of photobioreactor conduits, and
   coupling in said light along said areas of contact within said plurality of photobioreactor conduits to reach said algae.

20. The method of claim 19, wherein said at least one bioreactor module comprises a plurality of photo-bioreactor modules stacked on top of each other.

21. The method of claim 20, wherein said plurality of photo-bioreactor modules provide module-to-module fluid communication between respective ones of said plurality of photobioreactor conduits that are stacked on top of one another.

22. The method of claim 19, wherein said coupling in comprises fiber optic coupling.

23. The method of claim 19, further comprising controlling at least one of a gas concentration, a fluid flow, a temperature and a light level within said algae containment interior spaces.

* * * * *